USO05564423A

United States Patent [19]
Mele et al.

[11] Patent Number: 5,564,423
[45] Date of Patent: Oct. 15, 1996

[54] ULTRASONIC MEASUREMENT SYSTEM FOR THE DETERMINATION OF BONE DENSITY AND STRUCTURE

[75] Inventors: Ruggero Mele, Pordenone; Riccardo Isani, Castenaso; Ruggero Cadossi, Capri, all of Italy

[73] Assignee: IGEA S.r.l., Capri, Italy

[21] Appl. No.: 371,150

[22] Filed: Jan. 11, 1995

[30] Foreign Application Priority Data

Jan. 14, 1994 [IT] Italy ................................ TO94A0014

[51] Int. Cl.$^6$ ............................................. A61B 8/00
[52] U.S. Cl. .............................. 128/660.02; 128/661.03
[58] Field of Search ......................... 128/660.01, 660.02, 128/660.03, 660.06, 661.03; 73/597, 599

[56] References Cited

U.S. PATENT DOCUMENTS

| | | | |
|---|---|---|---|
| 3,847,141 | 11/1974 | Hoop | 128/660.01 |
| 4,612,656 | 9/1986 | Suzuki et al. | 377/24 |
| 4,802,487 | 2/1989 | Martin et al. | 128/662.06 |
| 4,913,157 | 4/1990 | Pratt, Jr. et al. | 128/661.03 |
| 5,119,820 | 6/1992 | Rossman et al. | 128/660.01 X |
| 5,396,891 | 3/1995 | Whitney et al. | 128/661.03 |

FOREIGN PATENT DOCUMENTS

| | | |
|---|---|---|
| 299906 | 1/1989 | United Kingdom . |
| 2067761 | 7/1991 | United Kingdom . |
| 2257253 | 1/1993 | United Kingdom . |
| 8707494 | 12/1987 | WIPO . |
| 9001903 | 3/1990 | WIPO . |

*Primary Examiner*—Francis Jaworski
*Attorney, Agent, or Firm*—Ladas & Parry

[57] ABSTRACT

Electronic system for measuring the density and structure of bone, in which an electronic central unit is equipped with ultrasonic calipers designed to be applied to a segment of the human body (for example, a finger) containing bone tissue to be examined. The central unit is designed to display on a screen an image of the ultrasonic signal transmitted through the bone tissue and highlight, on that image, two vertical marker lines correlated with the velocity with which the ultrasound signals are transmitted through the bone tissue and the velocity of transmission of the ultrasound signals through soft tissue. These vertical marker lines mark off the portion of the image that represents the ultrasonic signal received after passing through the bone tissue. The amplitude of this signal depends on the absorption of the ultrasound when passing through the bone tissue.

33 Claims, 8 Drawing Sheets

ULTRASONIC MEASUREMENT SYSTEM FOR THE DETERMINATION OF BONE DENSITY AND STRUCTURE

BACKGROUND OF THE INVENTION

This invention refers to an ultrasonic measurement system for determining the density and structure of bone.

There are known electronic systems for determining bone density, equipped with a first ultrasonic transducer designed to send multiple impulses into a body segment under examination (for example, a finger) and a second transducer designed to detect the impulses that actually pass through that body segment.

The known systems are further equipped with computer circuits that calculate the time elapsing between the emission of the impulse by the first transducer and its detection, and which calculate, on the basis of the known distance between the transducers, the velocity with which the ultrasounds pass through the body segment under examination.

The transmission velocity of the ultrasound signal is strongly influenced by the characteristics of the bone tissue placed between the transducers and varies with the variations in bone structure and density.

The known systems therefore compare the value of the measured velocity with a reference value, for the purpose of detecting a variation in the structure and density of the bone, which normally indicates decalcification of the bone tissue (caused, for example, by osteoporosis).

Comparison between the measured value and the reference value is not always adequate to permit an accurate examination, because the velocity with which the ultrasounds are transmitted through the tissue varies strongly from one subject to another or in a single subject if the measurement sites cannot be located repeatedly with great accuracy.

For this reason, the known systems do not permit an accurate or, especially, a reproducible examination.

SUMMARY OF THE INVENTION

The purpose of this invention is to create an ultrasonic measurement system for the determination of the density and structure of bone that will overcome the drawbacks of the known systems.

This purpose is fulfilled by the present invention, in that it pertains to a system such as the one described in claim 1.

BRIEF DESCRIPTION OF THE DRAWINGS

The invention will now be illustrated with specific reference to the attached drawings, which represent a preferred, but not exclusive, form of realization, in which.

DETAILED DESCRIPTION OF THE INVENTION

Figure 1:
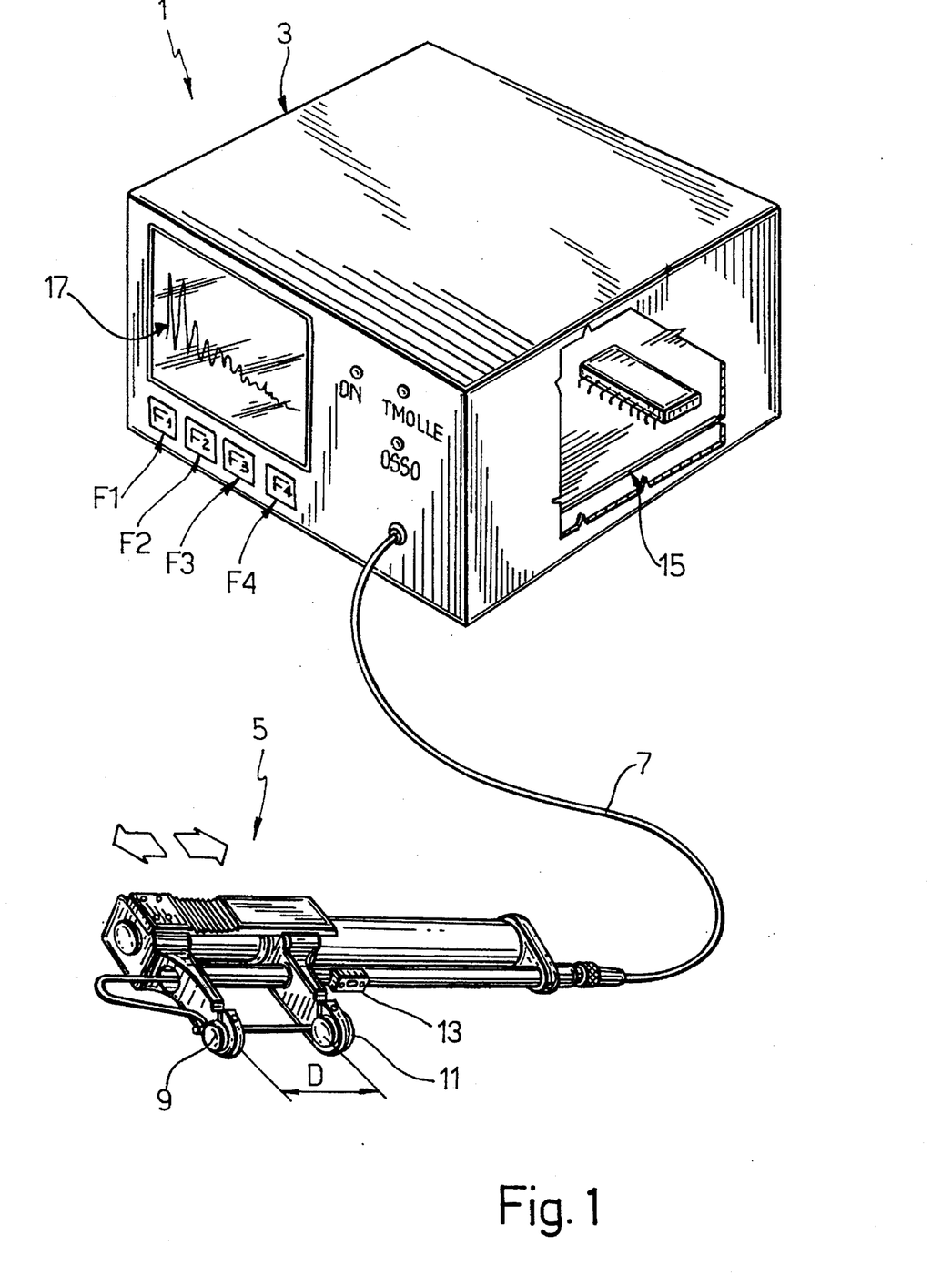
FIG. 1 illustrates an ultrasonic measurement system for the determination of the density and structure of bone.

In FIG. 1, the number 1 indicates, in its entirety, an ultrasonic measurement system for the determination of the density and structure of bone, in which an electronic central unit 3 is connected to ultrasonic calipers 5 by a flexible cable 7. The calipers 5 (shown below in greater detail) include an ultrasound-generating transducer 9 and an ultrasound-receiving transducer 11, placed so as to face one another and separated by a manually adjustable distance D. The calipers 5 are equipped with a linear position transducer, specifically a potentiometer (shown in detail below), designed to detect the value of distance D and to transmit the value thus detected to the central unit 3. The calipers 5 are also equipped with a button 13 (FREEZE) which, when pressed, is designed to send to the central unit 3 a command to temporarily memorize the signals arriving from the calipers 5.

The electronic central unit 3 includes a signal-generating circuit (not shown), designed to provide transducer 9 with a sequence of simple pulses (having a frequency, for example, ranging from 1 to 1.25 MHz) and a signal-receiving circuit (not shown) designed to receive the pulses received from the transducer 11. The electronic central unit 3 also includes a microprocessor computer circuit 15 designed to process the signals picked up from the receiver circuit (not shown).

The central unit 3 is equipped with a display device 17, appropriately consisting of a monochrome screen which is designed to display to a system user (not shown), by means that will be clarified below, the measurements calculated by the circuit 15. The central unit 3 is further equipped with four manually operable function keys, F1, F2, F3 and F4, which operate in conjunction with the circuit 15 for the selection of the functions performed by the system 1.

Figure 5A:
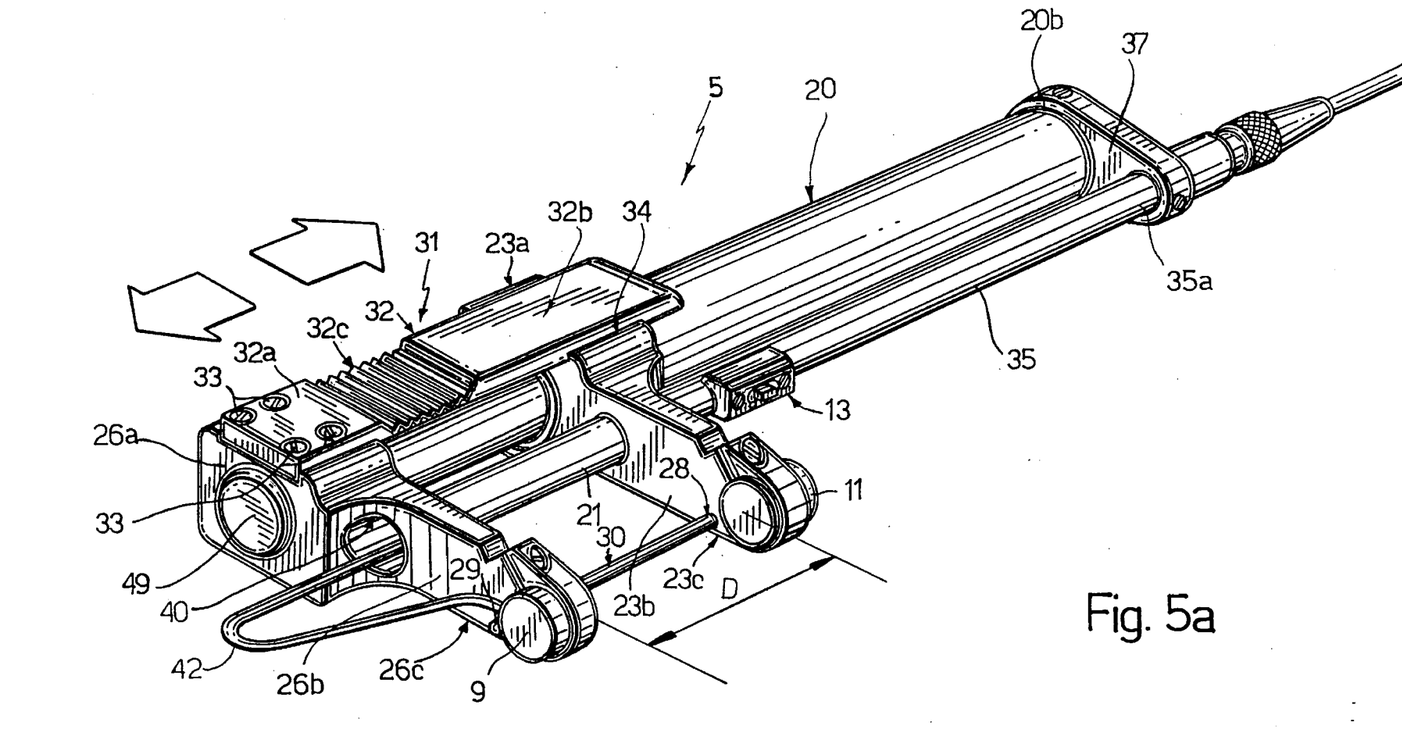
FIGS. 5a and 5b illustrate ultrasonic calipers used in the system represented by the present invention.
Figure 5B:
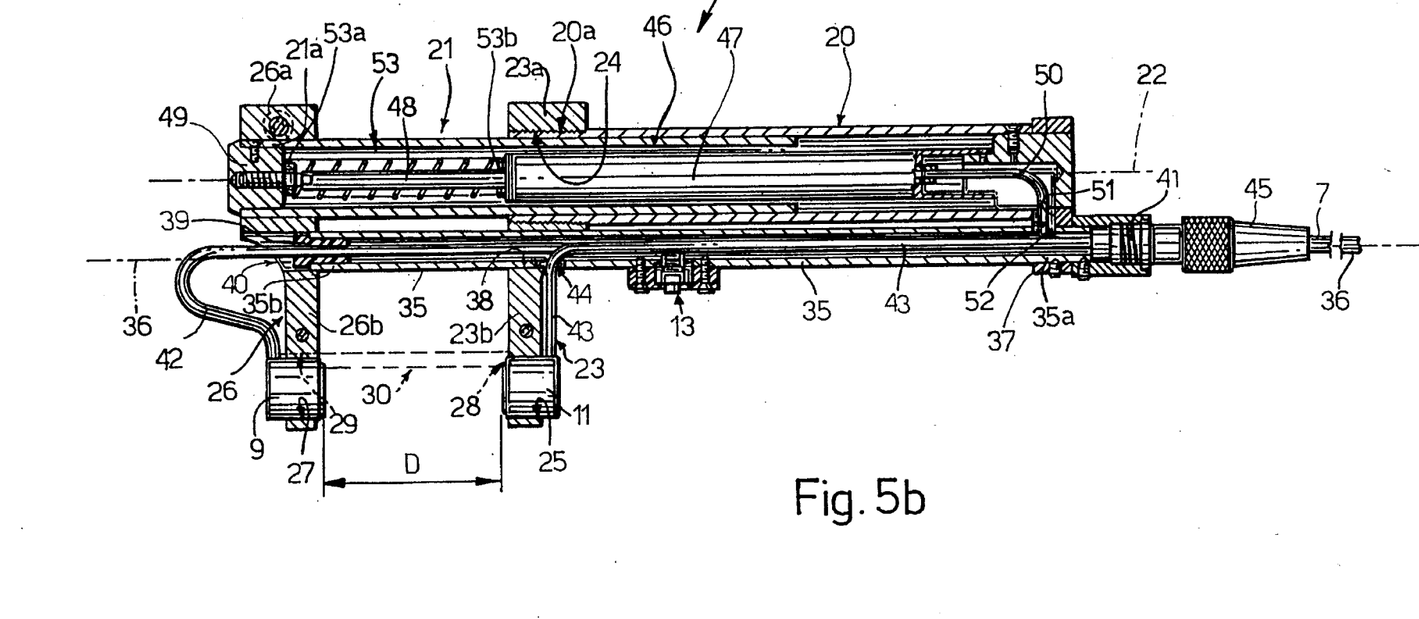

With reference to FIGS. 5a and 5b, the number 5 indicates, overall, the ultrasonic calipers 5 which comprise a first external tubular body 20, telescopically connected to a second internal tubular body 21. This body 21 is coaxial with body 20 and slides, with respect to the latter, along an axis 22.

The first tubular body 20 has a first threaded free end 20a, from which extends a first radial attachment 23, which includes a portion of a rectangular base 23a equipped with a threaded through hole 24 engaged by end 20a and a rectilinear portion 23b which extends radially from a portion of the base 23a. The rectilinear piece 23b, also has at one of its free ends a through hole, 25, which houses the transducer 11.

The second tubular body 21 extends for a certain distance beyond body 20 and terminates with a portion of end 21a that carries a second radial attachment 26, placed so as to face the first attachment 23 and including a portion of rectangular base 26a joined to end 21a and a rectilinear piece 26b that extends radially from the portion of base 26a. The rectilinear portion 26b has at one of its free ends a through hole, 27, which houses the ultrasound transducer 9 placed facing transducer 11 at a distance D from the latter.

The first and second attachments 23 and 26 have respectively a dead hole 28 and a through hole 29 placed in the vicinity of holes 25 and 27 respectively. Holes 28 and 29 are also close to a rectilinear border 23c, 26c of the attachment (FIG. 5a).

Bole 28 houses a portion of the end of a cylindrical rod 30 that extends between the first and the second attachments 23, 26, parallel to axis 22 and sliding through hole 29.

Rod 30 constitutes a element of verification that permits the correct positioning (by means to be clarified hereunder) of a portion of the human body, in particular a finger, with respect to attachments 23, 26 and to transducers 9, 11.

Hole 29 is so located that, when a finger is placed in the calipers with a part lying on rod 30, the bony portion of the finger is centered between transducers 9 and 11.

The calipers 5 are further equipped with a manual device 31 with which to set the distance D between the transducers 9 and 11.

Device 31 includes a rectangular plate 32 characterized by a first free end 32a, permanently affixed to a portion of the base 26a by four screws 33, and a second free end 32b seated in a rectangular groove 34 made in the base portion 23a. The plate 32 has a slightly curved shape and presses on the bottom portion (not shown) of groove 34.

The plate 32 is also equipped with a toothed middle part 32c. The calipers 5 are equipped with a tube 35 carried on body 20 and extending along an axis 36 parallel to axis 22. In particular, tube 35 is characterized by a first portion of end 35a carried on a radial flange 37 which is joined to a second end 20b of tubular body 20 and an intermediate portion that passes through a hole 38 realized in attachment 23 and coaxial with axis 36. The tube 35 also has a second portion of its end 35b in close proximity to portion 21a of body 21 and terminating with an opening plugged by a perforated stopper 39.

The portion of end 35b is also designed to pass through a hole 40 made in attachment 26 and coaxial with axis 36.

Tube 35 has at one end a base 41 from which issues a first cable 42 that extends inside tube 35 for the entire length of the aforesaid tube and passes through stopper 39, whence it arrives at transducer 9 after making an elbow bend (FIG. 5b).

Tube 35 also carries a second cable 43 which extends from base 41 to a through hole 44 in tube 35, through which cable 43 exits from the above tube 35 to reach transducer 11. Tube 35 also carries button 13, which is connected to base 41 by a cable (not shown) housed in tube 35.

A connector 45 is also screwed onto base 41, from which exits cable 7.

The calipers 5 are further equipped with a linear potentiometer 46 housed within the tubular bodies 20 and 21 and designed to detect the relative position of these bodies. Specifically, potentiometer 46 comprises an external tubular case 47 coaxially housed in tubular body 20 and comprising a resistor (not shown) along which runs a slider (not shown) connected to a first end (not shown) of a shaft 48, coaxial with axis 22 and presenting a second end screwed to a stopper 49 which closes the end portion 21a of tubular body 21.

The potentiometer 46 has an exit cable 50 that leaves the tubular body by way of a through hole 51 and penetrates tube 35 through a hole 52 in proximity to hole 51 and reaches base 41.

The calipers 5 are further-equipped with an elastic element 53 placed between tubes 20 and 21 and consisting of a helical extension spring housed coaxially in tube 21 and having portions of its ends 53a and 53b connected respectively to stopper 49 and to a portion of the end of tubular body 47.

This elastic element 53 is designed to generate a force tending to move attachments 23 and 26 closer together. In particular, spring 53 has a rigidity of approximately 400 newton/meter (or ranging from 300 to 500 newton/meter).

Figure 2A:
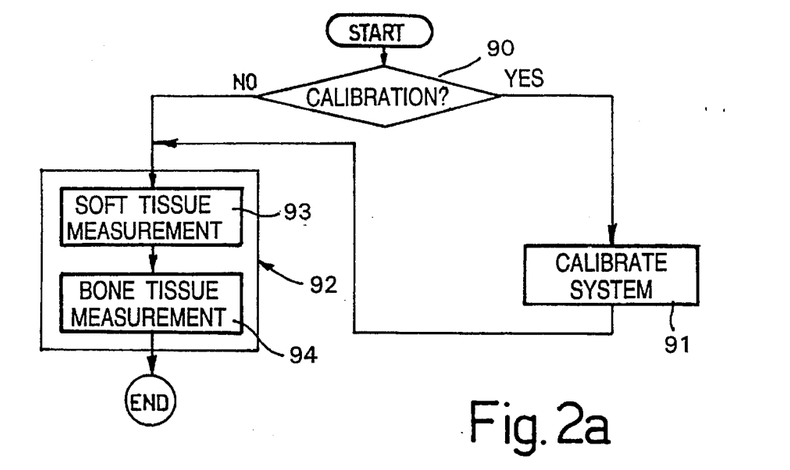
FIGS. 2a, 2b, and 2c are flow charts showing the function of the system illustrated in FIG. 1 broken down into logical blocks.

FIG. 2a specifically illustrates a flow chart of the operations performed by the electronic central unit 3.

The initial stage leads to a block 90 which asks and this question is displayed on the screen 17 whether the user wishes to calibrate the system or proceed instead to a measuring session.

In the former case, the next step leads to a block 91 which activates the process of calibrating the system in the known manner. Otherwise it leads to a block 92 which performs a set of operations designed to measure the density and structure of bone. Once the calibration process is completed, block 91 leads to block 92.

Block 92 includes a first block 93 (MEASURE SOFT TISSUE—described in detail hereunder), in which a set of measurements is performed on a portion of soft tissue of the human body, and a block 94 (MEASURE BONE TISSUE—described in detail hereunder), which follows block 93 and commands a set of measurements on a portion of bone tissue of the human body.

Specifically, in order to take the measurements illustrated in block 93, attachments 23 and 26 are separated from one another by manually operating device 31 and the elastic element 53 is wound up.

A portion of soft tissue of the human body is then placed between transducers 9 and 11; specifically, the interphalangeal space between the first and second finger of the hand (first intermetacarpal space), device 31 is released and attachments 23 and 26, propelled by the elastic element 53, come to rest against the portion of soft tissue with transducers 9 and 11 in contact with the skin 8 (with the possible interposition of gel).

In order to take the measurements diagrammed in block 94, the attachments 23 and 26 are separated from one another by manually operating device 31 and the elastic element 53 is wound up.

A proximal phalanx of the last four fingers of the hand is then placed between the transducers 9, 11 with the back of said phalanx resting on rod 30. In this position the transducers 9 and 11 are positioned in the metaphysical area in contact with the condyles.

The thickness of the bone tissue in this phalanx is predominant with respect to the thickness of the skin (soft tissue). For this reason, that portion of skin will be overlooked in the following description, since it is automatically taken into account by the measurement system 1.

Device 31 is released, and attachments 23 and 26, propelled by the elastic element 53, come to rest against opposite sides of the finger with the transducers 9 and 11 lying on opposite sides of the bone tissue (not shown) of the finger. In this position the finger (and therefore the bone tissue) is stably positioned with respect to the calipers 5 since it cannot move sideways owing to the impediment created by attachments 23 and 26 that are pressing against the sides of the finger. The calipers 5 cannot move downward, toward the palmar side of the hand because of the obstacle constituted by the rod 30. Nor can the calipers 5 move distally toward the second phalanx due to the anatomic impediment constituted by the condyles of the phalanges.

The positioning of the finger in the manner described above permits the correct positioning of the bone tissue in relation to the transducers 9 and 11 for all measurements performed.

Figure 2B:
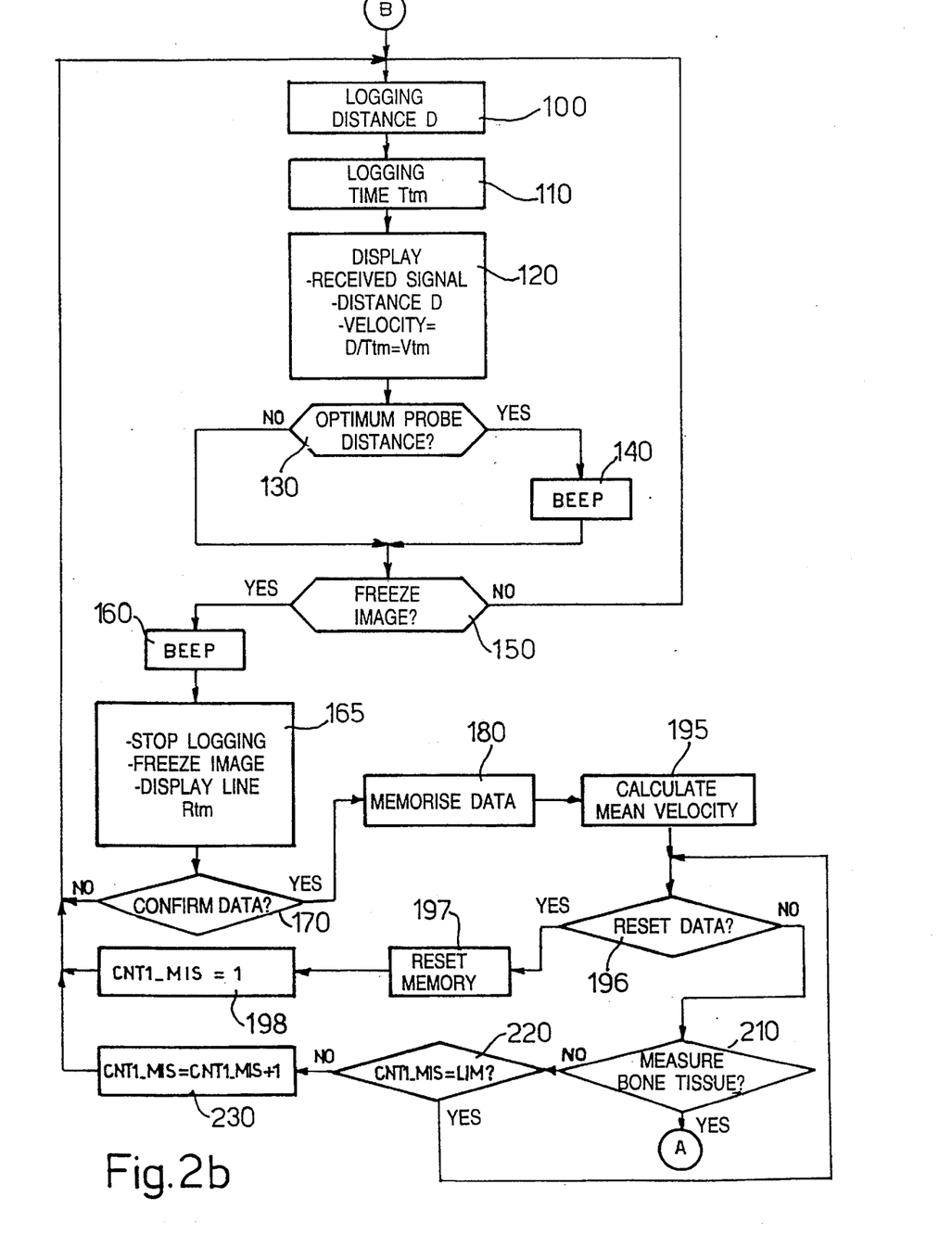

With specific reference to FIG. 2b, block 93 (SOFT TISSUE MEASUREMENT) includes a block 100 that automatically logs the distance D between the transducers 9 and 11.

Block 100 is followed by a block 110, in which the time Ttm elapsed between the generation of an impulse and the receiving of that impulse by transducer 11 is detected; block 110 therefore detects the time Ttm taken by the ultrasound signals to pass from transducer 9 to transducer 11 and through the portion of soft tissue lying between transducers 9 and 11.

Block 110 also calculates the velocity Vtm of the ultrasounds in the soft tissue as Vtm=D/Ttm.

Block 110 is followed by a block 120 in which the previously processed information is commanded to be displayed on the screen 17; specifically, block 120 commands the screen display of the value of distance D (THICKNESS) expressed in millimeters, the velocity of the ultrasound signal in the soft tissues (VELOCITY) expressed in meters per second, and the wave form of the ultrasound signal received by transducer 11.

Figure 4A:
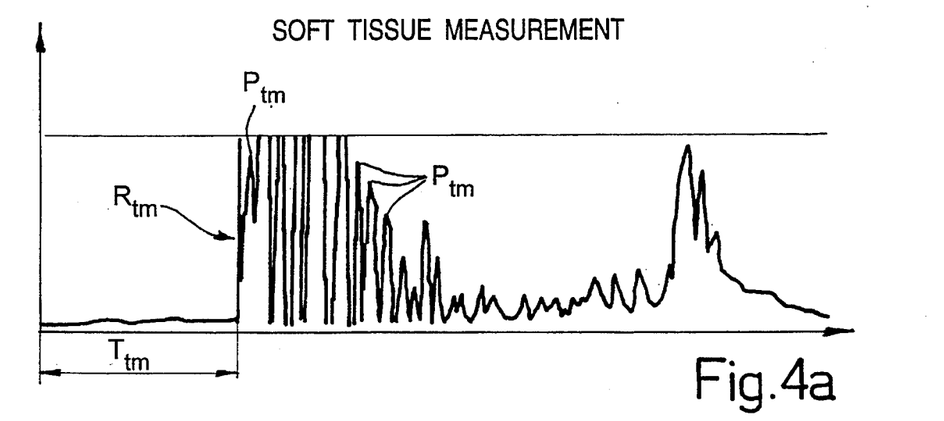
FIGS. 4a, 4b, 4c, 4d and 4e show some images displayed by the system represented by the present invention.

With specific reference to FIG. 4a, this figure illustrates an example of a Cartesian graph, displayed on the screen 17, of the wave form of the ultrasound signal received by transducer 11 and processed by the processor 15, in which the y-axis shows the amplitude of the signal received, and the x-axis shows the time scale. The received signal includes multiple successive peaks Ptm, of which the first peak to reach a reference amplitude is used to calculate the time Ttm and the subsequent peaks are due to the reflections of the impulse through the walls of the soft tissue.

Block 120 is followed by a block 130, in which the current value of distance D is compared with a reference value $D=D_{threshold}$ corresponding to an optimum distance for measurement; if the distance D corresponds to the threshold $(D=D_{threshold})$, the flow chart leads from block 130 to a block 140 that commands the emission of an acoustic signal (BEEP) to denote the attainment of the optimum distance. If distance D does not correspond to the threshold, block 130 leads directly to block 150, which is in any case the point of arrival after block 140.

Block 150 awaits a command for the temporary memorization of the image displayed on the screen 17; if this command is not given, block 150 leads back to block 100, otherwise (button 13 pressed) it leads to a block 160 which commands the emission of an acoustic signal (BEEP). Block 160 is followed by a block 165 that implements the temporary memorization of the wave form displayed on the screen 17, corresponding to the signal received from transducer 11. Specifically, the data relating to the on/off state of the points (pixels) that form the image displayed on the screen are memorized in a transitional memory (BUFFER) (not shown) and the image of the wave form is thus "frozen" (FREEZE).

Block 165 further commands the display on the screen of a vertical marker line Rtm (FIG. 4a) placed in a position corresponding to the first predetermined amplitude peak of the signal displayed on the screen 17. The distance Ttm of this line Rtm from the origin of the time scale therefore represents the time required by the ultrasound signal to pass through the soft tissue.

Block 165 is followed by a block 170 which awaits a command confirming memorization of the data related to the "frozen" wave form; if the operator wishes to request this permanent memorization, he presses function key F1 (confirm data) and block 170 then leads to a block 180 which executes the permanent memorization of the data. Otherwise the operator again presses button 13, the contents of the buffer are deleted and block 170 leads back to block 100.

Block 180 permanently memorizes, for example in a RAM memory (not shown), the velocity of the ultrasound signal in soft tissue, the distance D and the wave form logged in the preceding measurement.

Block 180 is followed by a block 195 which calculates the mean Vm of the velocities memorized from previous measurements.

Block 195 is followed by a block 196 which awaits a command to reset the data currently logged; if the operator wishes to reset the data, he presses function key F2 (reset data) and block 196 then leads to a block 197. Otherwise (confirm data), block 196 is followed by a block 210.

Block 197 performs the total deletion of the data logged (RESET MEMORY) and is followed by a block 198.

Block 198 re-initializes the counter CNT1_MIS, that is (CNT1_MIS=1); block 198 then leads back to block 100.

Block 210 asks, and this query is displayed on the screen 17, whether the operator wishes to take another measurement of soft tissue. If so, the operator presses function key F2 (soft tissue) and block 210 then leads to a block 220; otherwise the operator presses function key F3 (bone tissue) and block 210 leads back to block 94.

In block 220, the contents of counter CNT1_MIS are compared with a pre-defined value, for example three; if the value of the counter is equal to the predefined value (CNT1_MIS=pre-defined value), block 220 leads back to block 196. Otherwise it leads to a block 230.

Block 230 increases the contents of counter CNT1_MIS by one unit, using the logical operation CNT1_MIS= CNT1_MIS+1; and the chart returns from block 230 to block 100. It is thus possible to perform multiple measurements on soft tissue, up to the threshold value of the counter CNT1_MIS, and to gather a corresponding number of data sets (distance D, velocity V, wave form) that are memorized in succession at block 180.

Specifically, block 180 memorizes, in memory addresses distinct from RAM memory, the velocity values V1, V2 and V3 detected in successive measurements, and block 195 calculates the mean Vm of the velocities (V1, V2, V3) memorized in successive measurements.

Figure 2C:
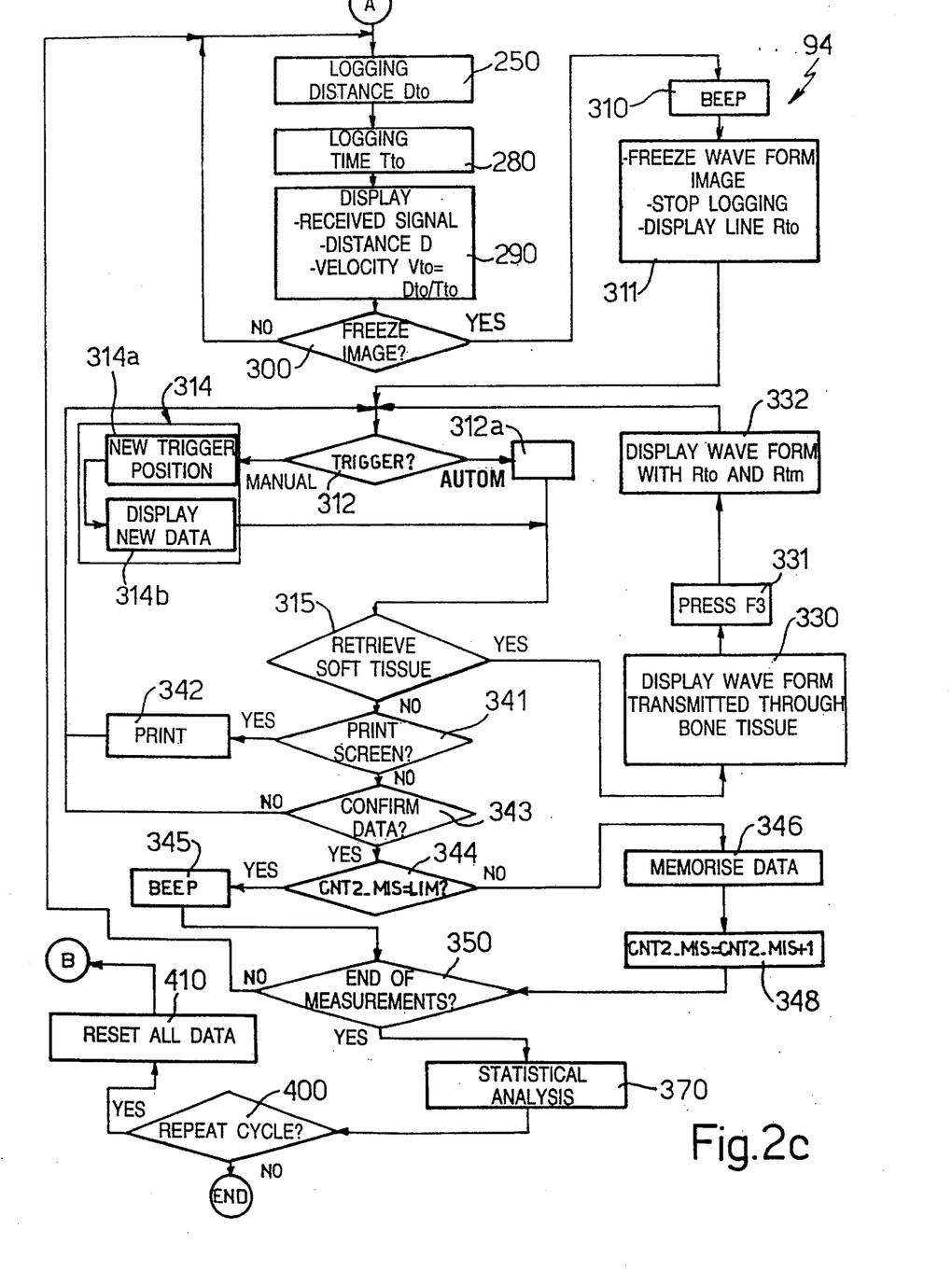

With specific reference to FIG. 2c, block 94 includes block 250 which performs the automatic gathering of data relating to the distance D between the transducers 9 and 11.

Block 250 is followed by a block 280, in which the time Tto elapsed between the generation of an impulse and the detection of the first predetermined amplitude peak of the impulse received by transducer 11 is detected. Block 280 thus detects the time Tto required by the ultrasound signal to move from transducer 9 to transducer 11 and to pass through the portion of bone tissue lying between transducers 9 and 11.

Block 280 is followed by a block 290 that calculates the velocity Vto of the ultrasounds in bone tissue as Vto=D/Tto. Block 290 commands the display on the screen 17 of the information previously processed; in particular, block 290 commands the screen display of the value of distance D (THICKNESS) expressed in millimeters, the velocity of the ultrasound signal in the bone tissues (VELOCITY) expressed in meters per second, and the wave form of the ultrasound signal transmitted through the bone tissue and detected by transducer 11.

Figure 4B:
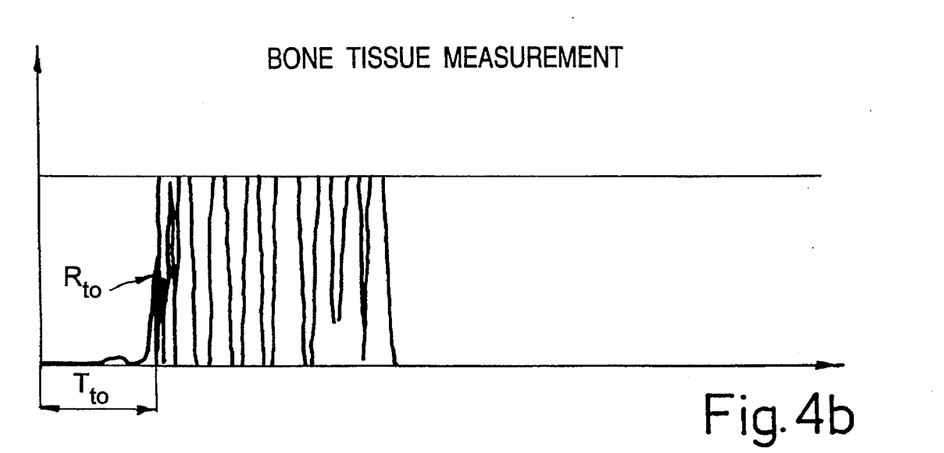

With specific reference to FIG. 4b, this figure illustrates an example of a Cartesian graph of the wave form of the received ultrasound signal, in which the y-axis shows the amplitude of the signal received, and the x-axis shows the time scale.

Block 290 is followed by a block 300 that awaits a command for the temporary memorization of the image on the screen 17; if this command is not given, block 300 leads back to block 250, otherwise ("FREEZE" key pressed) it leads to a block 310 which commands the emission of an acoustic signal (BEEP). Block 310 is followed by a block 311 that implements the memorization of the wave form displayed on the screen 17. Specifically, the data relating to the on/off state of the points (pixels) that constitute the wave form in the image displayed on the screen are memorized in a transitional memory (BUFFER) (not shown) and the image of the wave form is thus "frozen" (FREEZE).

Block 311 also commands the display on the screen of a vertical marker line Rto (FIG. 4b) placed in a position corresponding to the first amplitude peak displayed on the screen. The distance Tto of this line Rto from the origin of the time scale therefore represents the time required by the ultrasound signal to pass through the soft tissue.

Block 311 is followed by a block 312 in which the mode of signal detection is selected.

In block 312, an automatic signal-detection mode (AUTOMATIC TRIGGER) (block 312a) is automatically selected. In this mode of selection any received signal that displays on screen 17 a reference amplitude greater than a pre-established number of dots (pixels), for example 32 pixels, is recognized as the first significant peak.

In addition, at block 312 it is possible to manually select a block 314 that commands a substantially manual mode of detection (MANUAL TRIGGER) in which any received signal that displays on screen 17 a reference amplitude greater than a manually set number of pixels is recognized as the first peak. Block 314 includes a first block 314a that commands the manual selection of the reference amplitude and a block 314b that commands the re-positioning of the vertical marker line Rto placed in a position corresponding to the detected peak on the basis of the previously established reference amplitude.

Blocks 314 and 312a are followed by a block 315 in which the operator is asked if he wishes to retrieve the data relating to the soft tissues; in the affirmative case, block 315 leads to a block 330; otherwise it leads to block 341.

Block 330 displays on the screen (FIG. 4c) the wave form of the ultrasound signal S transmitted through the bone tissue and the line Rtm, both previously memorized.

Block 330 is followed by a block 331 in which the pressing of function key F3 (bone tissue) is awaited.

Block 331 is followed by a block 332 which displays on the screen (FIG. 4c) the wave form of the ultrasound signal S transmitted through the bone tissue, line Rto and line Rtm. Since the velocity of the ultrasound passing through soft tissue is always less than its velocity through bone tissue, line Rtm is farther from the origin of the time scale than line Rto.

Figure 4C:
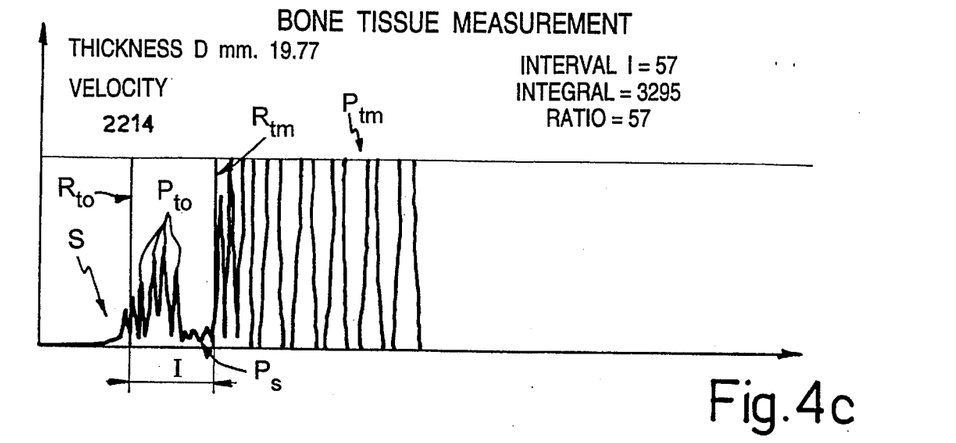

The portion of the signal S shown on the screen 17 and included in the interval between lines Rto and Rtm therefore represents the ultrasound signal received after passing through the bone tissue- Marker lines Rto and Rtm provide for defining on the signal on screen 17 the limits of an "observation window" containing signal portion S. Specifically, block 332 calculates the integral of the signal S shown on the screen 17 in the interval I that falls between lines Rto and Rtm, and displays the value of that integral and of interval I on the screen. Block 332 also calculates and shows on the screen 17 the ratio between the value of the integral and the amplitude of the interval I. It is also possible to analyze the incremental ratios between the amplitudes of the peaks that fall between the two marker lines Rto and Rtm and to generate, on the basis of all the parameters calculated, a summary index (SONIC INDEX) whose numeric value describes the density and structure of the bone tissue.

Block 332 then leads back to block 312.

In block 341 the operator is asked if he wishes to print the data shown on the screen 17; if so, the operator presses function key F2, in which case block 341 leads to a block 342; otherwise it leads to a block 343.

Block 342 commands the printing of the data currently shown on the screen 17; block 342 is then followed by block 312.

Block 343 awaits a command Confirming the permanent memorization of the data relating to the wave form shown on the screen 17. If the operator wishes to perform this permanent memorization, he presses function key F1 (confirm data), and block 343 leads to a block 344; otherwise the operator once again presses button 13 (data not confirmed) and block 343 leads back to block 312.

In block 344, the contents of counter CNT2_MIS are compared with a pre-defined threshold, for example four; if the value of the counter is equal to the threshold (CNT1_MIS=threshold), block 344 leads to a block 345. Otherwise it leads to a block 346.

Block 346 performs the permanent memorization, for example in a RAM memory (not shown), of the set of data shown by blocks 330 and 332, that is the velocity of the ultrasound signals in bone tissue and in soft tissue, the distance D, the size of interval I, the value of the integral, the ratio between the integral and the interval I and the wave form of the signal transmitted through the bone tissue.

Block 346 is followed by a block 348 that increases the contents of counter CNT2_MIS by one unit, using the logical operation CNT2_MIS=CNT2_MIS+1; block 348 then leads to a block 350.

Block 345 commands an acoustic signal (BEEP) and is also followed by block 350.

Block 350 asks, and this query is displayed on the screen 17, whether the operator wishes to take another measurement of bone tissue. If so, the operator presses function key F3 (another bone tissue measurement) and block 350 then leads back to block 250; otherwise (end of measurement) the operator presses function key F2 and block 350 leads to a block 370.

From the above description, it will be understood how it is possible to perform multiple measurements on different bones (for example, the first phalanges of the last four fingers of the hand) up to the threshold value of the counter CNT2_MIS, and gather a corresponding number of data sets.

The data shown on the screen 17, from blocks 330 through 332, make it possible to immediately and accurately evaluate the condition of the analyzed bone tissue and to highlight possible pathologies of that bone tissue.

Specifically, it is possible to recognize a bone of low density due to osteoporosis.

FIG. 4c shows a typical signal S curve detected in a "healthy" bone, not affected by pathological conditions of any kind.

The velocity observed through the bone tissue is equal to 2214 meters per second, the breadth of the interval I (measured during presentation of soft tissue) is 57 pixels, the value of the integral is 3295 and the ratio between the integral and the interval I is 57. Lines Rto and Rtm mark off a portion of the signal in which multiple Pto peaks (bone tissue peaks) are present, exhibiting a smaller amplitude than the Ptm peaks (soft tissue peaks) that follow line Rtm.

Between the Pto peaks and the Ptm peaks, there is a zone of separation $P_5$ of lesser amplitude.

Figure 4D:
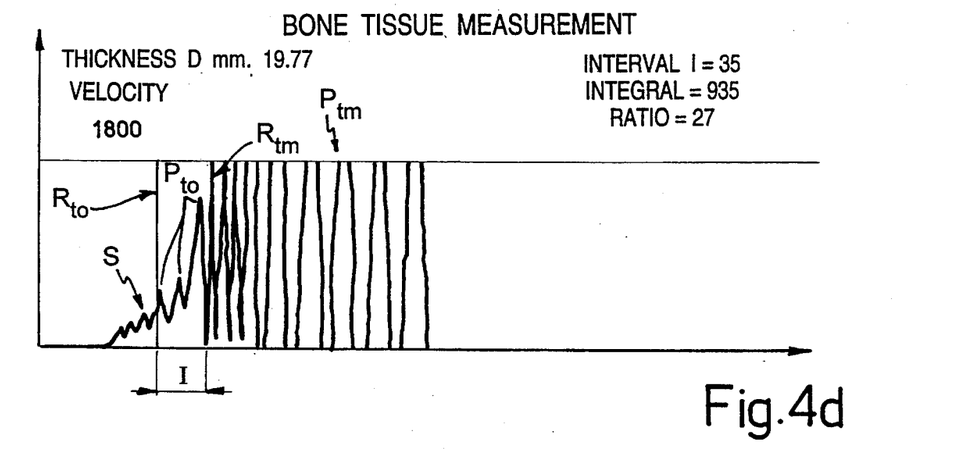

FIG. 4d shows a typical signal S curve detected in a "pathological" bone suffering from osteoporosis.

The velocity observed through the bone tissue is equal to 1800 meters per second (considerably lower than that observed in healthy bone tissue), the breadth of the interval I (measured during presentation of soft tissue) is 35 pixels, the value of the integral is 953 and the ratio between the integral and the interval I is 27.

Lines Rto and Rtm and much closer together than in the previous example.

It can be clearly seen, also, that there is no area of separation between the Pto peaks and the Ptm peaks.

Block 370 (described in detail below) performs a statistical analysis of the data observed and is followed by a block 400 in which the operator is asked whether he wishes to perform a new cycle of measurements. If the answer is affirmative, block 400 leads back to block 100, after having reset all the data memorized in a block 410. Otherwise the program exits.

Figure 3:
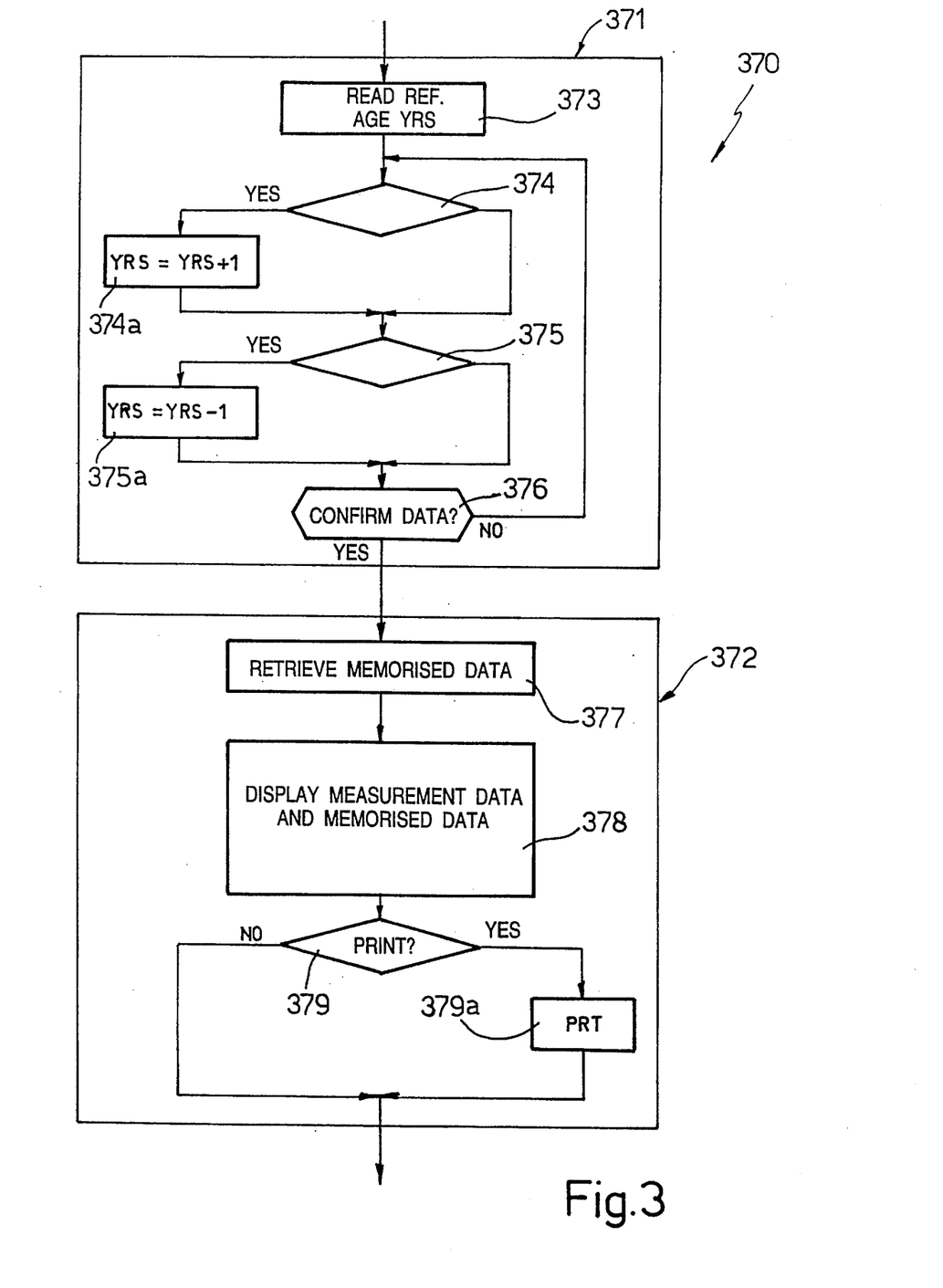
FIG. 3 details a single block of the flow chart illustrated in FIG. 2C.

FIG. 3 shows a detail of block 370 which performs the statistical analysis on the data detected during the previous measurements.

Block 370 comprises an initial block 371, which enters the age of the subject on whom the measurement is being performed, and a second block 372 in which the data measured for the subject, as a function of age, are compared with previously memorized statistical data.

Block 371 comprises a first block 373, which is designed to read from a memory (not shown) the numerical value corresponding to a reference age YRS, for example fifty years, YRS=50; block 373 is also designed to display this age value YRS on the screen 17 (FIG. 3a).

Block 373 is followed by a block 374 that awaits a command to increase by one unit the current value of YRS; if the operator wishes to increase the YRS value he presses function key F1 and block 374 leads to a block 374a. Otherwise he presses no key and block 374 leads to block 375.

Block 374a increases the age value by one unit, using the logical operation YRS=YRS+1; block 374a also leads to a block 375.

Block 375 awaits a command to decrease the current value of YRS by one unit; if the operator wishes to decrease the YRS value he presses function key F2 and block 375 leads to a block 375a. Otherwise he presses no key and block 375 leads to a block 376.

Block 375a decreases the age value by one unit, using the logical operation YRS=YRS−1; block 375a also leads to a block 376.

Block 376 awaits a command to confirm the current YRS value; if the operator wishes to confirm this age value he presses function key F3, and block 376 leads to block 372. Otherwise the operator presses function key F4 and block 376 leads back to block 374.

Block 372 comprises a first block 377 in which multiple previously memorized data are recalled. These data express a graph which shows the curve of the velocity of transmission of the ultrasound signals through bone tissue as a function of age.

Figure 4E:
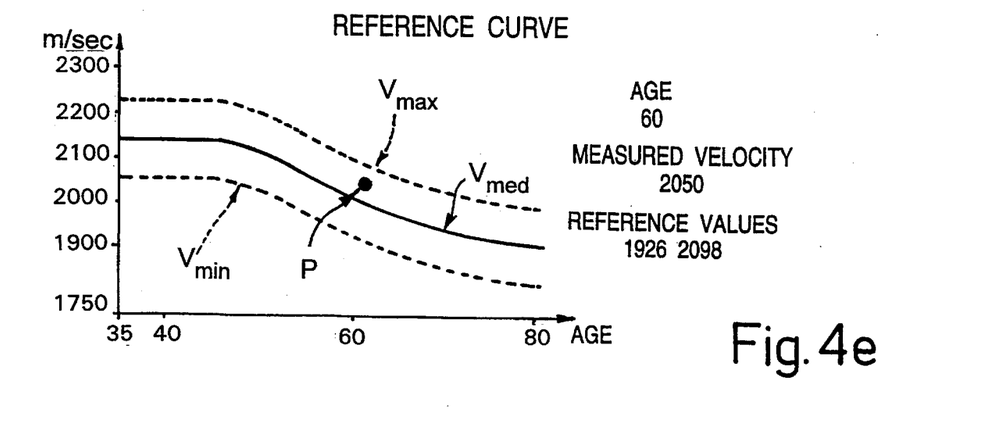

With specific reference to FIG. 4e, block 377 commands a Cartesian graph in which increasing age values (from 35 to 80 years) are indicated on the x-axis and velocity values are indicated on the y-axis (expressed in meters per second). The graph includes a first curve Vmax which represents the trend, as a function of age, of the maximum velocity values observed in a reference population, a second curve Vmin that represents, as a function of age, the trend of the minimum velocity values observed in the reference population, and a third curve Vmed that represents the trend, as a function of age, of the mean velocity values observed in the reference population.

Block 377 is followed by a block 378 in which a velocity value for bone tissue measured in block 94 is recalled; this value is shown as a point P on the Cartesian plane as a function of the age set in block 371.

Specifically, if this value falls between the Vmax and Vmin curves, it may be presumed that the subject on whom the analysis was performed presents no pathologies of any kind, whereas if the velocity of the ultrasound is lower (points below the Vmin curve, showing low bone density) the subject is probably suffering from osteoporosis.

Block 378 is further followed by a block 379 in which the operator is asked if he wishes to print the statistical data thus processed and displayed on the screen 17; if the answer is affirmative, block 379 leads to a block 379a that commands a printer (not shown) connected to the central unit 3; otherwise it leads directly to block 400.

A comparison is later made between the calculated index (SONIC INDEX) and a memorized reference index.

From the above description it will be clear that the system realized in the present invention overcomes the drawbacks of the known systems.

This system in fact makes it possible to calculate and display not only the velocity of ultrasound signals in bone tissue, but also the velocity of ultrasound in soft tissue, and also permits the joint display of these data (blocks 330 and 332), thus providing the user of the system with images of the sort described above and illustrated in FIGS. 4c and 4d.

These images provide multiple information not provided by the known systems.

Diagnosis in bone tissue is therefore performed by observing:

the value of the velocity in bone tissue;

the amplitude of interval I falling between the marker lines Rto and Rtm;

the value of the integral calculated in block the wave form of the signal falling between the marker lines Rto and Rtm;

the reference index (SONIC INDEX) that sums up multiple data in a single numeric value.

From the above observations it will be clear that the above-described system provides multiple information that is not provided by the known systems, and therefore permits a more accurate diagnosis.

The statistical analysis commanded in block 370, moreover, permits a rapid and immediate comparison of the observed data with the reference data.

It is clear, finally, that changes and variations may be made in the described system without departing from the protected sphere of the invention.

The transducers 9 and 11 could have a different placement from that illustrated in FIG. 5a: for example, transducers 9 and 11 could be placed side by side and carried on the same attachment or integrated in a single case.

We claim:

1. Ultrasonic measuring system for determining the density and structure of bone, comprising:

an electronic control unit, ultrasonic calipers connected to said electronic control unit and including first and second transducers, the first transducer being a generator of ultrasound signals and the second transducer a receiver of said ultrasound signals, said transducers facing one another at an adjustable spacing therebetween, said calipers being constructed to accommodate a segment of the human body placed between said first and second transducers, said electronic unit comprising electronic means for determining from said ultrasound signals the time taken by the ultrasound signals to pass through the segment of the human body from said first transducer to said second transducer, said electronic means comprising:

first electronic calculation means for producing a first measurement of the ultrasound signal passing through a first segment of soft tissue of the human body and for calculating a first time period (Ttm) taken by said ultrasound signal to pass through said first segment, second electronic calculation means for producing a second measurement of the ultrasound signal passing through a second segment of the human body, which includes bone tissue to be examined, and for calculating a second time period (Tto) taken by said ultrasound signal to pass through said second segment, electronic processing means receiving ultrasound signals produced by said second electronic calculation means in said second measurement, for producing output signals to present on a display device of said electronic unit a wave form of said ultrasound signal detected by said second electronic means jointly with said first time period (Ttm) and said second time period (Tto), said signals from said electronic processing means defining on said display device at least limits (Rto, Rtm) of an observation window containing a portion (S) of said ultrasound signal detected by said second electronic means, said portion (S) of said ultrasound signal representing the ultrasound signal received following passage through said second segment and being indicative of density and structure of the bone tissue under examination.

2. System as described in claim 1, wherein said second segment consists of the distal metaphysis of the first phalanx of the last four fingers of the hand on the lateromedial plane.

3. System as described in claim 1, wherein said signals produced by said electronic processing means produce on said display a Cartesian graph of said wave form having axes on which are represented, respectively, time and amplitude of the received signals, said signals produced by said electronic processing means further producing on said display together with said wave form, a first marker (Rto) and a second marker (Rtm) in respective positions corresponding to said first and second time periods (Ttm, Tto) and marking off a portion of the wave form representing the signal transmitted through said second segment of the human body.

4. System as described in claim 3, wherein said signals produced by said electronic processing means include amplitude of an interval (I) between said first marker (Rto) and said second marker (Rtm) to show said amplitude on said display device.

5. System as described in claim 3, wherein said electronic processing means calculates an integral of the portion (S) of the signal in an interval (I) between the first marker (Rto) and the second marker (Rtm) for display on said display device the value of said integral.

6. System as described in claim 5, wherein said electronic processing means calculates a ratio of said integral to the amplitude of said interval (I) for display on said display device.

7. System as described in claim 3, wherein said electronic processing means calculates a ratio of the amplitudes of signal peaks falling between said first marker (Rto) and said second marker (Rtm) and generating a summary index (SONIC INDEX) having a numerical value which describes the density and structure of the examined bone tissue.

8. System as described in claim 3, wherein said first electronic calculation means includes:

electronic means for at least temporarily freezing the wave form of the ultrasound signal detected by said first electronic calculation means, to show on said display device said first marker (Rtm) in a position corresponding to a first peak of the wave form of the ultrasound signal detected by said first electronic means.

9. System as described in claim 3, wherein said second electronic calculation means includes:

electronic means for freezing, at least temporarily, the wave form of the ultrasound signal detected by said second electronic means for showing on said display device, (a) said second marker (Rto) in a position corresponding to a first peak of the wave form of the ultrasound signal detected by said first electronic means and (b) said first marker (Rto) of said wave form.

10. System as described in claim 1, wherein said first electronic calculation means comprises:

electronic means for determining the spacing between said transducers, further electronic means for displaying said spacing on said display device, comparison means for comparing the value of said spacing with a reference value corresponding to an optimum spacing for measurement, said comparison means emitting a signal if the measured spacing is substantially equal to said reference value.

11. System as described in claim 1, wherein said first electronic calculation includes:

electronic means for repeating, for a preestablished number of cycles, measurements taken on the first segment of the human body to calculate a multiple number of first time periods (Ttm).

12. System as described in claim 11, comprising further electronic means for calculating a mean value of said multiple first time periods (Ttm).

13. System as described in claim 1, wherein said second electronic calculation means includes:

electronic means for detecting said second time period (Tto) when a first peak of the received ultrasound signal exceeds a threshold value, said electronic means including means for manually setting said threshold value and means for automatically selecting said threshold value.

14. System as described in claim 1, wherein said first electronic calculation means calculates velocity of the ultrasound signal passing through said first segment, and said second electronic calculation means calculates velocity of the ultrasound signal passing through said second segment.

15. System as described in claim 14, further comprising statistical analysis means for comparing a value detected for the velocity of the ultrasound signals passing through said second segment with reference values.

16. System as described in claim 15, wherein said statistical analysis means includes electronic means for showing on said display device a Cartesian graph of previously memorized reference curves, in which said Cartesian graph has axes, respectively representing increasing age values and increasing velocity values and for displaying on said Cartesian graph a comparison result representing a velocity value calculated by said second electronic calculation means and a manually-set age value.

17. System as described in claim 1, wherein said calipers include:

a first tubular body, a second tubular body coaxial with the first tubular body and slidable axially with respect thereto, a first rectilinear attachment extending radially from a portion of an end of said first tubular body, a second rectilinear attachment extending radially from a portion of an end of said second tubular body, said first and second attachments being positioned to face one another and carrying said first and second transducers at said spacing which is adjustable as a function of a relative position of said first and second tubular bodies.

18. System as described in claim 17, wherein said first attachment has at one of its free ends a hole within which said first transducer is housed, said second attachment having at one of its free ends a hole within which said second transducer is housed.

19. System as described in claim 17, further comprising means for setting the relative position of second tubular body with respect to said first tubular body and including an elongated metal plate having a first end joined to an end of one of said tubular bodies and a second flat end placed in contact with one portion of the other of said tubular bodies.

20. System as described in claim 17, further including elastic means placed between said first and second tubular bodies to generate a force tending to move said attachments closer together.

21. System as described in claim 20, wherein said elastic means comprises a helical spring having a rigidity of approximately 400–500 newton/meter.

22. System as described in claim 17, further including electrical means for measuring the relative position of said second body with respect to said first body.

23. System as described in claim 22, wherein said electrical means includes potentiometric means interposed between said tubular bodies.

24. System as described in claim 23, wherein said potentiometric means includes sliding means carried on said second tubular body and resistor devices carried on said first tubular body.

25. System as described in claim 24, wherein said potentiometric means further includes a casing for said resistor means housed in said first body and a shaft that moves said sliding means, said shaft being coaxial with said second tubular body and having one end connected to said second body.

26. System as described in claim 17, further including a third tubular body extending parallel to said first and second tubular bodies, a middle portion of said third tubular body passing through a hole provided in said first attachment and having a portion of its end passing through a hole provided in said second attachment, said third tubular body containing and guiding exit cables from said ultrasound transducers.

27. System as described in claim 17, further including means for precisely positioning a portion of the human body, comprising the phalanx of a finger, in relation to said attachments and to said transducers.

28. System as described in claim 27, wherein said means for precisely positioning the portion of the human body includes a movable cylindrical rod that extends between said first and second attachments parallel to said first and second tubular bodies.

29. Diagnostic method for the determination of density and structure of bone comprising the following steps:

applying electronic calipers on a portion of soft human tissue, said calipers being equipped with at least one ultrasound transducer and one ultrasound receiver, detecting and memorizing a velocity at which ultrasound signals pass through said portion of soft tissue, applying said electronic calipers on a portion of human tissue containing at least bone tissue to be examined, detecting and memorizing a velocity at which ultrasound signals pass through said bone tissue, displaying a wave form of the ultrasound signals transmitted through said bone tissue, displaying a first marker (Rto) and a second marker (Rtm) on said wave form, in correlation with said velocity (Ttm, Tto) of the measured ultrasound signals passing respectively through said bone tissue and said soft tissue, said markers (Rto, Rtm) defining a portion of the wave form representing the ultrasound signal received after passing through the bone tissue and indicative of bone density and structure of said bone tissue.

30. Method as described in claim 29, wherein said second portion of the human body contains a distal metaphysis of the first phalanx of the last four fingers of the hand on the lateromedial plane.

31. Diagnostic method for the determination of the density and structure of bone as described in claim 29, wherein said step of displaying said markers on said wave form (Rto, Rtm) includes the step of detecting the amplitude of an interval (I) between the aforesaid second marker (Rto) and said first marker (Rtm), and the step of calculating, in said interval (I), the integral of said wave form signal.

32. Diagnostic method for determining the density and structure of bone comprising the following steps:

placing a pair of transducers on a first portion of the human body consisting principally of soft tissue, providing an excitation impulse to a first of said transducers, receiving, by the second of said transducers an ultrasound signal transmitted through said first portion of the human body, calculating the time (Ttm) taken by the ultrasound signal to pass through said first portion of the human body, calculating the velocity of the ultrasound signal passing through said first portion of the human body, placing said pair of transducers on a second portion of the human body containing bone tissue to be examined, providing an excitation impulse to said first transducer, receiving, by said second transducer an ultrasound signal transmitted through said second portion containing said bone tissue, measuring the distance between said transducers, calculating the time taken by the ultrasound signal to traverse said bone tissue (Tto), calculating the velocity at which said ultrasound signal passes through said bone tissue, showing on a display device a wave form of the ultrasound signal transmitted through said bone tissue, correlating said wave form with a time period (Ttm) taken by the ultrasound signal to pass through said first portion of the human body and with a time period (Tto) taken by the ultrasound signal to traverse said bone tissue, and wherein the step of placing the pair of transducers on a first portion of the human body includes the step of placing between said transducers a proximal phalanx of the last four fingers of the hand with the back of the phalanx placed downward on a positioning device, and positioning said transducers in the metaphyseal area in contact with the condyles.

33. Diagnostic method for the determination of the density and structure of bone as described in claim 32, comprising determining an interval in said ultrasound signal passing through said second portion of the human body represented by the difference between the velocity of said first and second signals, and evaluating the bone tissue under examination based on said signal in said interval.

* * * * *

UNITED STATES PATENT AND TRADEMARK OFFICE
CERTIFICATE OF CORRECTION

PATENT NO. : 5,564,423
DATED : October 15, 1996
INVENTOR(S) : Ruggero Mele, et al.

It is certified that error appears in the above-indentified patent and that said Letters Patent is hereby corrected as shown below:

On title page, item 75, "Capri" should be -- Carpi --.

Signed and Sealed this

Twenty-ninth Day of July, 1997

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,564,423
DATED : October 15, 1996
INVENTOR(S) : Ruggero Mele, et. al.

It is certified that error appears in the above-identified patent and that said Letters Patent is hereby corrected as shown below:

On title page, item [73] "Capri" should be -- Carpi --

Signed and Sealed this

Seventh Day of April, 1998

Attest:

BRUCE LEHMAN

Attesting Officer     Commissioner of Patents and Trademarks